US009416160B2

(12) United States Patent
Blareau et al.

(10) Patent No.: US 9,416,160 B2
(45) Date of Patent: Aug. 16, 2016

(54) MACROMOLECULAR COMPLEX OF BACTERIAL ORIGIN AND USE OF SAID MACROMOLECULAR COMPLEX FOR PREVENTING AND TREATING INFLAMMATORY RHEUMATISM

(75) Inventors: Jean-Pierre Blareau, Steenvoorde (FR); Michel Colavizza, Roeulx (FR); Frederic Huguet, Lille (FR); Charles Romond, La Madeleine (FR)

(73) Assignee: BIFINOVE, Lille (FR)

( * ) Notice: Subject to any disclaimer, the term of this patent is extended or adjusted under 35 U.S.C. 154(b) by 354 days.

(21) Appl. No.: 13/808,701

(22) PCT Filed: Jul. 5, 2011

(86) PCT No.: PCT/FR2011/051593
§ 371 (c)(1),
(2), (4) Date: Feb. 5, 2013

(87) PCT Pub. No.: WO2012/004522
PCT Pub. Date: Jan. 12, 2012

(65) Prior Publication Data
US 2013/0130988 A1    May 23, 2013

(30) Foreign Application Priority Data

Jul. 5, 2010   (FR) .................................... 10 55432

(51) Int. Cl.
| | | |
|---|---|---|
| *C12P 19/04* | (2006.01) | |
| *C12P 1/04* | (2006.01) | |
| *C07K 14/00* | (2006.01) | |
| *C12N 1/00* | (2006.01) | |
| *C07K 14/195* | (2006.01) | |
| *A23L 1/30* | (2006.01) | |
| *A23L 1/305* | (2006.01) | |
| *A61K 38/16* | (2006.01) | |
| *C12N 1/20* | (2006.01) | |

(52) U.S. Cl.
CPC ............. *C07K 14/195* (2013.01); *A23L 1/3014* (2013.01); *A23L 1/3058* (2013.01); *A61K 38/164* (2013.01); *C07K 14/00* (2013.01); *C12N 1/00* (2013.01); *C12N 1/20* (2013.01); *C12P 1/04* (2013.01); *C12P 19/04* (2013.01); *A23V 2002/00* (2013.01)

(58) Field of Classification Search
None
See application file for complete search history.

(56) References Cited

U.S. PATENT DOCUMENTS

| | | |
|---|---|---|
| 8,197,826 B2 | 6/2012 | Petay et al. |
| 2008/0038776 A1 | 2/2008 | Romond et al. |
| 2008/0057109 A1* | 3/2008 | Collins et al. ................. 424/439 |

FOREIGN PATENT DOCUMENTS

| | | |
|---|---|---|
| WO | 2004/093898 A2 | 11/2004 |
| WO | 2006/040485 A2 | 4/2006 |

OTHER PUBLICATIONS

New Riverside University Dictionary, The Riverside Publishing Company, p. 933, 1984.*
International Search Report, dated Oct. 28, 2011, from corresponding PCT application.
Barbara Sheil et al., "Modulation of the commensal flora by probiotic feeding delay the onset and decreases the severity of disease in the collagen-induced arthritis (CIA) model in a strain-dependent manner", XP-002620173; Cited in International Search Report, 2007.
Takuya Suzuki et al., "Inhibition of Bacterial Translocation from the Gastrointestinal Tract of Mice by Oral Administration of a Culture Condensate of Bifidobacterium longum", J. Vet. Med. Sci., 1997, pp. 665-669, vol. 59, No. 8, XP-002620174; Cited in International Search Report.
S. Menard et al., "Lactic acid bacteria secrete metabolites retaining anti-inflammatory properties after intestinal transport", Gut, Jun. 1, 2004, pp. 821-828, vol. 53, No. 6, XP-008046639; Cited in International Search Report.
Borja Sanchez et al., "Exported proteins in probiotic bacteria: adhesion to intestinal surfaces, host immunomodulation and molecular cross-talking with the host", FEMS Immunol. Med. Microbiol., 2008, pp. 1-17, vol. 54, XP-002620175; Cited in International Search Report.

* cited by examiner

*Primary Examiner* — S. Devi
(74) *Attorney, Agent, or Firm* — Young & Thompson

(57) ABSTRACT

A bacterial macromolecular complex produced by bacteria belonging to the *Bifidobacterium longum* strain deposited according to the treaty of Budapest under number CNCM I-3994 with the Collection Nationale de Cultures de Microorganismes (CNCM) [National Collection of Microorganism Cultures], consisting of chains combining a lipoprotein and an oligosaccharide, wherein:
the lipoprotein has a molecular weight of from 30 kDa to 60 kDa;
the oligosaccharide has a molecular weight of less than 15 kDa, and preferably less than 10 kDa;
the lipoprotein component, which consists of all the lipoproteins of each of the chains, represents from 75 to 99%, preferentially from 80 to 98%, more preferentially from 85 to 95% by weight of the total weight of the complex, and the oligosaccharide component, which consists of all the oligosaccharides combined with each of the chains, represents from 1 to 25%.

18 Claims, 6 Drawing Sheets

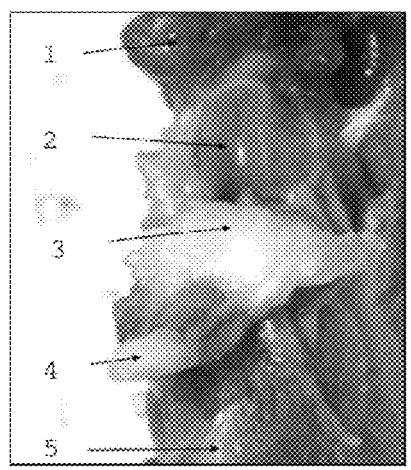
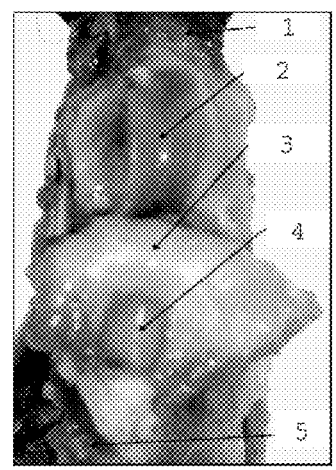
Figure 6a    Figure 6b
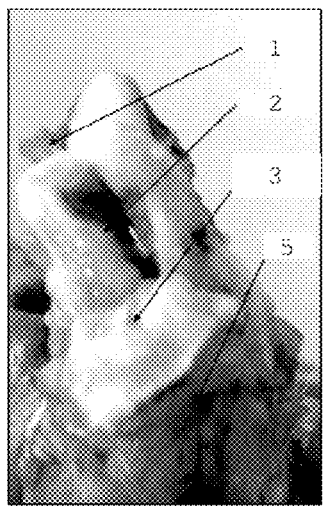
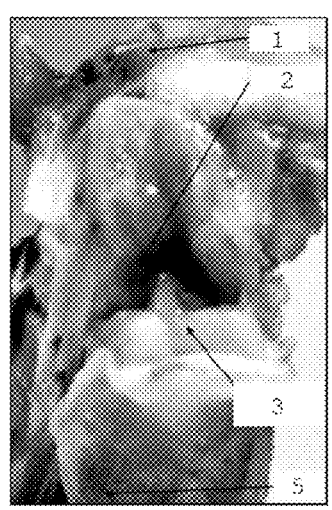
Figure 7a    Figure 7b
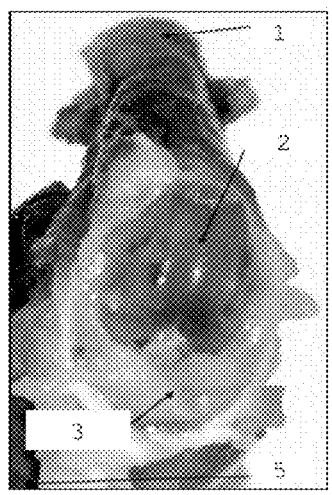
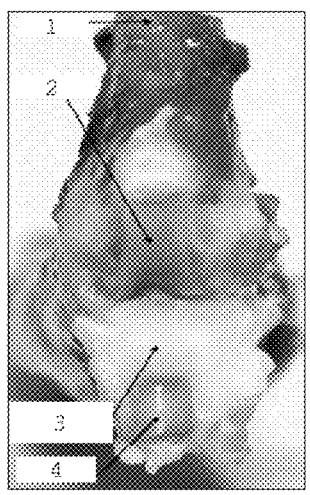
Figure 7c    Figure 7d

| Genes | Nomenclature | FA vs FNV* FC | FA vs FA+** FC | function |
|---|---|---|---|---|
| | | | | Metabolism |
| Carboxypeptidase B1 (tissue) (Cpb1), mRNA [NM_029706] | Cpb1 | 309.50 | -252.30 | protein degradation |
| Carboxypeptidase A1 (Cpa1), mRNA [NM_025350] | Cpa1 | 87.14 | -217.03 | protein degradation |
| Carboxypeptidase A2, pancreatic (Cpa2), mRNA [NM_001024698] | Cpa2 | 6.92 | -6.60 | protein degradation |
| Mus musculus RIKEN cDNA 2210010C04 gene, mRNA [NM_023333] | 2210010C04Rik | 100.41 | -133.44 | protein degradation (trypsinogen-like activity) |
| protease, serine, 1 (Prss1), mRNA [NM_011645] | Prss1 | 16.55 | -17.25 | protein degradation (inflammatory response) |
| protease, serine, 3 (Prss3), mRNA [NM_011645] | Prss3 | 6.58 | -8.46 | protein degradation (inflammatory response) |
| peptidase, serine | peptidase, serine | 8.73 | -17.17 | peptide hydrolysis |
| Chymotrypsin C (caldecrin) (Ctrc), mRNA [NM_010338875] | Ctrc | 15.54 | -30.45 | protein degradation |
| protease, serine | 1810049H19Rik | 8.23 | -12.17 | protein degradation |
| protease, serine, 2 (Prss2), mRNA [NM_009431] | Prss2 | 5.34 | -12.95 | protein degradation |
| carboxyl ester lipase (Cel), mRNA [NM_009885] | Cel | 18.09 | -12.20 | lipid degradation |
| pancreatic lipase related protein 1 (Pnliprp1), mRNA [NM_018874] | Pnliprp1 | 108.58 | -177.37 | lipid degradation |
| pancreatic lipase (Pnlip), mRNA [NM_026925] | Pnlip | 95.10 | -138.79 | lipid degradation |
| PANCREATIC TRIGLYCERIDE LIPASE (FRAGMENT) homolog [Rattus norvegicus] | Pnlip | 19.13 | -49.96 | lipid degradation |
| amylase 1, salivary (Amy1), mRNA [NM_007446] | Amy1 | 88.72 | -125.11 | sugar hydrolysis |
| amylase 1, salivary (Amy1), mRNA [NM_007446] | Amy1 | 29.38 | -23.27 | sugar hydrolysis |
| | | | | Immune response, inflammation |
| elastase 2A (Ela2a), mRNA [NM_007919] | RP23-394H4.4 | 24.725 | -23.922726 | inflammatory diseases (emphysema, sarcoidosis) |
| Riken clone:C230027D20 product:mitogen activated protein kinase 10, [AK082242] | Mapk10 | 22.987818 | -22.56085 | immune response - Ag presentation |
| deleted in malignant brain tumors 1 (Dmbt1), mRNA [NM_007769] | Dmbt1 | 3.7283275 | -4.3291807 | immune response - Ag presentation, receptor G++ bacteria |
| PREDICTED: Mus musculus similar to keratin associated protein 9-1 (LOC432600), mRNA [XM_484079] | OTTMUSG00000002193 | 22.03008 | -22.150348 | immune response? Keratin protein kinase |
| ribonuclease, RNase A family, 1 (pancreatic) (Rnase1), mRNA [NM_011271] | Rnase1 | 14.073265 | -16.946436 | apoptosis, maturation of dendritic cells derived from monocytes |
| myeloblastosis oncogene-like 1 (Mybl1), mRNA [NM_008651] | Mybl1 | 9.542029 | -13.389937 | cell division (CDC25B, MYBL1), hyperplasia of the spleen expansion of B lymphocytes |
| clone:A930089811 product:unclassifiable, full insert sequence [AK139458] | AK139458 | 15.529197 | -15.187141 | Ig-like |
| FK506 binding protein 5 (Fkbp5), mRNA [NM_010220] | Fkbp5 | 5.7161316 | 5.996187 | glucocorticoid receptors, binding to dexamethasone |

\* comparison of gene expressions of dendritic cells of arthritic patient flora-associated mice vs healthy volunteer flora-associated mice.

\*\* comparison of gene expressions of spleen dendritic cells of arthritic patient flora-associated mice treated for 15 days with 0.2 mg/l of molecules vs nontreated mice.

Table 6 : Genes of which the expression is restored to the expression values in human flora-associated mice.

Figure 8

| Genes | Nomenclature | FAt vs FA** FC | Metabolism | function |
|---|---|---|---|---|
| Colipase, pancreatic (Clps), mRNA [NM_025469] | Clps | -49.773 | lipid metabolism | |
| Amylase 2, pancreatic (Amy2), mRNA [NM_009669] | Amy2 | -696.162 | sugar metabolism | |
| Extra cellular link domain-containing 1 (Xlkd1), mRNA [NM_053247] | Xlkd1 | | | lymphatic vessel endothelial hyaluronan receptor 1 (LYVE1): internalization of hyaluronic acid, catabolism of glycosaminoglycan |
| Galactose-3-O-sulfotransferase 2 (Gal3st2), mRNA [NM_199366] | Gal3st2 | -3.015 | | sulfation Gal in position C3 (mucin) |
| | | -3.021 | | |
| | | | Immune response/inflammation | |
| 10 days neonate cerebellum cDNA, RIKEN full-length enriched library, clone:B930094O12 | AK081163 | -11.095 | prostaglandin reductase 2 : mode of action of indomethacin by binding to PGTR2 | decrease = reduction in inflammation |
| Cell division cycle 25 homolog B (S. pombe) (Cdc25b), mRNA [NM_023117] | Cdc25b | -4.500 | initiation of mitosis | entry into cell division (in association with PROK2, PRSS3 (includes EG:5646)) |
| Endothelin receptor type B (Ednrb), mRNA [NM_007904] | Ednrb | -5.601 | excretion of proteins and of sodium, quantity of Ca2+ (in association with AMY2A, CEL, CPC, PNLP, PROK2) endothelial dysfuntion endocrine system disorder (in association with AMY2A, CEL, CPC, PNLP, PROK2) | |

Table 7 : Genes of which the expression is modified only with treatment

Figure 9

MACROMOLECULAR COMPLEX OF BACTERIAL ORIGIN AND USE OF SAID MACROMOLECULAR COMPLEX FOR PREVENTING AND TREATING INFLAMMATORY RHEUMATISM

FIELD OF THE INVENTION

The present invention relates to a macromolecular complex of bacterial origin and also to the use of said macromolecular complex for the prophylaxis and treatment of inflammatory rheumatism.

BACKGROUND OF THE INVENTION

Many scientific studies have demonstrated the role played by the intestinal flora in the pathogenesis of chronic rheumatic inflammatory diseases such as rheumatoid arthritis, ankylosing spondylitis or post-infectious rheumatism.

For example, no signs of arthritis are observed in germ-free animals (transgenic rats or mice), whereas their littermates harboring intestinal flora develop signs of arthritis (Rath H C, et al; *J. Clin. Invest;* 98(4); 945-953; 1996 and Abdollahi-Roodsaz S., et al; *J. Clin. Invest;* 118; 205-216; 2008).

Moreover, in human beings, studies have shown that patients in whom rheumatoid arthritis was recently diagnosed harbored few bifidobacteria, compared with control subjects (Vaahtovuo J, et al; *J. Rheumatol;* 35; 690-693; 2008) and, when the equilibrium of the intestinal flora was partially restored by introducing a vegetarian diet, the patient's condition was found to be improved (Peltonen R, et al; J. *Rheumatol;* 36; 64-68; 1997). Finally, it is well known that the use of certain antibiotics which modify the composition of the intestinal flora improves the signs of rheumatoid arthritis (Stone M. et al.; *J. Rheumatol;* 30; 2112-2122; 2003).

One of the mechanisms which explains the involvement of the intestinal flora in the pathogenesis of chronic rheumatic diseases lies in its ability to regulate bacterial translocation. The mechanism of bacterial translocation is defined as the crossing of the intestinal barrier by intestinal bacteria. These intestinal bacteria are taken up and then transported by cells of the intestinal immune system, such as dendritic cells or macrophages, to the synovial site, causing a source of painful inflammation of rheumatic type in the joints.

The composition of the intestinal flora has an influence on this process. Thus, when bifidobacteria widely colonize the lower part of the intestine, they show an ability to reduce bacterial translocation (Romond M B, et al.; *Anaerobe;* 14; 43-48; 2008).

Moreover, the composition of the intestinal flora also has an influence on the expression level of genes involved in the inflammatory response, such as galectins (Romond M B, et al; *Fems Immunol Med Microbiol;* 55; 85-92; 2009).

There are at the current time many products capable of modifying the intestinal flora, such as prebiotics or probiotics. On the other hand, few of them have a positive impact on bacterial translocation. Among the products which have a beneficial action with respect to bacterial translocation, is the macromolecule isolated from *Bifidobacterium breve* culture. Indeed, it has been demonstrated, in documents WO 2004/093898 and WO 2006/040485, that the oral administration of this macromolecule leads to a decrease in translocation and in bacterial dissemination, and that the said molecule exhibits a preventive activity against collagen-induced arthritis in mice. However, a residual pro-inflammatory activity is always observed with the use of the macromolecule isolated from *Bifidobacterium breve* culture, thereby limiting its use in the field of inflammatory diseases.

It would therefore be advantageous to have a product which enables a decrease in bacterial translocation to be obtained and which would not exhibit any residual pro-inflammatory activity.

As it happens, the applicant has discovered that the use of a macromolecular complex isolated from *Bifidobacterium longum* complex makes it possible to satisfy these requirements.

SUMMARY OF THE INVENTION

The macromolecular complex of the present invention is produced by the *Bifidobacterium longum* CBi0703 strain, deposited according to the treaty of Budapest under number CNCM I-3994 in the name of BIFINOVE, on May 23, 2008, with the Collection Nationale de Cultures de Microorganismes (CNCM) [National Collection of Microorganism Cultures] held by the Institut Pasteur, 25 rue du docteur Roux 75015 Paris.

Said macromolecular complex consists of chains combining a lipoprotein and an oligosaccharide, within which:
- the lipoprotein has a molecular weight of 30 kDa to 60 kDa;
- the oligosaccharide has a molecular weight of less than 15 kDa, and preferably less than 10 kDa;
- the lipoprotein component, which consists of all the lipoproteins of each of the chains, represents from 75 to 99%, preferentially from 80 to 98%, more preferentially from 85 to 95% by weight of the total weight of the complex, and the oligosaccharide component, which consists of all the oligosaccharides linked to each of the chains, represents from 1 to 25%, preferentially from 2 to 20%, and more preferentially from 5 to 15% of the total weight of the complex.

DETAILED DESCRIPTION OF THE INVENTION

The macromolecular complex comprises several chains combining a lipoprotein and an oligosaccharide, said chains being identical or different in nature. It is necessary, according to the invention, for the macromolecular complex comprising several chains to be in agglomerated form in order for an anti-arthritic effect to be observed. Indeed, the administration of low-molecular-weight (typically about 15 to 50 kDa) monomeric structures in mice has led to a significant increase in the arthritic score.

The macromolecular complex according to the invention must therefore necessarily have a molecular weight of greater than 150 kDa, preferably greater than 400 kDa and particularly preferably greater than or equal to 600 kDa.

According to the invention, the lipoprotein comprises the amino acid sequence SEQ ID No. 1:

*MTNVRVIKPALAALVAAAACVGGLAFSSAQPAQADTYSDLINAQNQHAASVQREAELKQ*

*QLAGASQDLANKVLELDDLTNNKIVAAQAKVTQANEDAATAQDEADAASGRLSAAQKDK*

*ETLEEQIKQTGKDYDDAHAAVAQLARDEMHGSNASDVMSVVTGATSTQDFVNSMQSRDA*

*LSRNEANAASSAATSLSTSKNRGERLAAIEKQIAVLKTQADEKAAPHRPPPK.*

The amino acid sequence of the lipoprotein is SEQ ID No. 2:

MTNVRVIKPALAALVAAAACVGGLAFSSAQPAQADTYSDLINAQNQHAASVQREAELKQ

QLAGASQDLANKVLELDDLTNNKIVAAQAKVTQANEDAATAQDEADAASGRLSAAQKDK

ETLEEQIKQTGKDYDDAHAAVAQLARDEMHGSNASDVMSVVTGATSTQDFVNSMQSRDA

LSRNEANAASSAATSLSTSKNRGERLAAIEKQIAVLKTQADEKAASAQTAAETAQSERD

ALDKLRQEGEARRDELSSMIDSLDSQSAKQAAQTVLIASQVDSYNRQFQKEQQDAANRV

DTGNQGGTPSTPVTPAPAPAPAPAPAPAPAPAPSVGGQGTSNGDYGNAYATGQCTYWAY

ERRRQMGIGTPSYLGNGGDWWRNAPSYGLRVDHNPQVGAALSFLPGQDGADGTWGHVAV

VEAVYGDGTFQISEMNVGGLWMMNYRTLTNLGQYWFVH.

The saccharides constituting the oligosaccharide component of macromolecular complex of the present invention can be chosen from galactose (Gal), N-acetylgalactosamine (Gal Nac), glucose (Glc), N-acetylglucosamine (Glc Nac), rhamnose (Rham) and mannose (Man), and mixtures thereof.

According to the invention, the weight ratio of sugar which is part of the composition of the macromolecule is from 1% to 25%, preferably from 2% to 20% and even more preferentially from 5% to 15%.

The average weight composition of galactose is between and 50 µg/mg of macromolecular complex, preferably between 5 and 20 µg/mg of macromolecular complex, and of mannose is between 0.5 and 10 µg/mg of macromolecular complex, preferably between 1 and 10 µg/mg of macromolecular complex; that of glucose is between 3 and 80 µg/mg of macromolecular complex, preferably between 5 and 50 µg/mg of macromolecular complex, and even more preferentially between 10 and 50 µg/mg of macromolecular complex; that of N-acetylgalactosamine is between 2 and 30 µg/mg of macromolecular complex, preferably between 2 and 20 µg/mg of macromolecular complex, and even more preferentially between 2 and 10 µg/mg of macromolecular complex; that of N-acetylglucosamine is between 1 and 10 µg/mg of macromolecular complex, preferably between 1 and 5 µg/mg of macromolecular complex; that of rhamnose is between 0.05 and 10 µg/mg of macromolecular complex, preferably between 0.05 and 5 µg/mg of macromolecular complex, and even more preferentially between 1 and 5 µg/mg of macromolecular complex.

The lipids constituting the lipid component of the macromolecular complex of the present invention can be chosen from the group consisting of long $C_{14}$, $C_{16}$ and $C_{18}$ saturated fatty acids, and mixtures thereof.

Moreover, it has been shown that this macromolecular structure is recognized by galectin-1 and TLR-6, which indicates, firstly, that galactose units are in an external position accessible to the galectin-1 receptor (galectin-1 recognizing the galactose present in lactose, and especially the galactose in an external position present in glycoconjugates) and, secondly, that the macromolecular complex retains lipoprotein units which can be recognized by the lipoprotein-specific subunit of the TLR2/6 complex.

The tests carried out by the Applicant have shown that the administration of said macromolecular complex induces anti-arthritic activity in mice, in a model of collagen-induced arthritis.

This anti-arthritic activity has been demonstrated through several observations:
  an improvement in the transcriptomic response of dendritic cells to bacterial translocation in mice associated with a biotope of a patient suffering from arthritis;
  conditioning of these dendritic cells leading to a co-evolution with the population of regulatory T lymphocytes responsible for the production of interleukin-10 (cytokine which has an important role in immunomodulation in the digestive system and which has in particular anti-inflammatory effects).

The macromolecular complex according to the invention is obtained by means of a method comprising the following steps:
  (i) inoculation and incubation for 16 to 60 h, under anaerobic conditions and at a temperature between approximately 30° C. and 39° C., of a *Bifidobacterium longum* strain deposited according to the treaty of Budapest under the number CNCM I-3994 with the Collection Nationale de Cultures de Microorganismes (CNCM) [National Collection of Microorganism Cultures] in a culture medium comprising a native or hydrolyzed whey protein fraction, lactose and an antioxidant;
  (ii) separation of said bacteria from said culture medium;
  (iii) ultrafiltration of the supernatant on filtration membranes which have a cut-off threshold of from 10 to 100 kDa, resulting in the obtaining of a concentrated retentate;
  (iv) enrichment with macromolecular complex by washing with a volume of from 5 to 50 times the volume of the concentrated retentate;
  v) purification of the macromolecular complex by molecular sieve chromatography under sterile conditions, for example on SUPERDEX® 200 gel;
  (vi) recovery of the excluded fraction which comprises the bacterial macromolecular complex.

It is important to prevent oxidation during the method, hence the need to introduce an antioxidant such as ascorbic acid, cysteine hydrochloride or thioglycollate.

According to one embodiment, the culture medium also contains other compounds, such as potassium dihydrogen phosphate involved in stabilizing the pH.

According to one embodiment, the inoculation of the bifidobacteria into said culture medium can be carried out using a frozen concentrate or a 16-24 h preculture, which enables proliferation of the bacteria.

According to another embodiment that can be combined with the previous one, the bacteria are inoculated into said culture medium in a proportion of $10^5$-$10^{10}$ colony-forming units per ml of medium.

According to one preferred embodiment of the invention, the culture medium comprises 1 to 20 g/l of medium of native or hydrolyzed whey proteins, 30 to 80 g/l of medium of lactose and 0.1 to 0.5 g/l of medium of ascorbic acid.

According to another preferred embodiment of the invention, the culture medium comprises 1 to 20 g/l of medium of native or hydrolyzed whey proteins, 30 to 80 g/l of medium of lactose, 0.1 to 0.5 g/l of medium of ascorbic acid and 0.5 and 3 g/l of medium of potassium dihydrogen phosphate.

According to one embodiment which can be combined with the previous ones, the pH of said culture medium is not regulated during the incubation.

Finally, according to another embodiment, the pH of said culture medium is maintained between 4 and 7 during the incubation.

The invention relates to the use of the macromolecular complex of bacterial origin according to the invention for preventing and treating joint disorders, and for regulating the intestinal flora and bacterial translocation.

According to another aspect, a subject of the present invention is the use of said macromolecular complex of bacterial origin obtained according to the method described previously, in products intended for the pharmaceutical, food-processing and/or nutraceutical industry.

A subject of the invention is in particular a pharmaceutical composition comprising at least said macromolecular complex, as active ingredient, and at least one pharmaceutically acceptable support.

The weight concentration of said macromolecular complex represents from 0.1 µg/g to 50 µg/g of the pharmaceutical composition.

The term "pharmaceutically acceptable" is intended to mean any support which makes it possible not only to preserve the immunomodulatory properties of the macromolecular complex obtained according to the method described previously, but also to carry said macromolecular complex.

The use of the pharmaceutical composition makes it possible to regulate the intestinal flora and bacterial translocation. It is consequently intended for the prophylaxis and treatment of inflammatory rheumatism, such as rheumatoid arthritis and ankylosing spondylitis, of osteoarthritis and of fibromyalgia.

The invention therefore relates to the use of the pharmaceutical composition for obtaining a medicament intended for regulating the intestinal flora and bacterial translocation.

Thus, the invention relates to a pharmaceutical composition for use in regulating the intestinal flora and bacterial translocation.

The invention also relates to the use of the pharmaceutical composition for obtaining a medicament intended for treating or preventing inflammatory rheumatism, osteoarthritis and fibromyalgia.

Thus, the invention relates to a pharmaceutical composition for use in the treatment and prevention of inflammatory rheumatism, osteoarthritis and fibromyalgia.

The invention also relates to the use of the pharmaceutical composition for obtaining a medicament intended for treating rheumatoid arthritis and ankylosing spondylitis, osteoarthritis and fibromyalgia.

Thus, the invention relates to a pharmaceutical composition for use in the treatment of rheumatoid arthritis and ankylosing spondylitis, osteoarthritis and fibromyalgia. The pharmaceutical composition of the present invention can be in any galenical form desired for administration either orally to humans or to animals, for instance in liquid form (syrup, solution, spray) or solid form (powder, tablet, gel capsule, capsule, spray powder, gum, paste, granules, in their various forms, for immediate or programmed release), or rectally, nasally, via the pulmonary route, or parenterally, or in a form suitable for administration by inhalation or insufflation. The preferred administration mode is generally oral administration.

The pharmaceutical composition comprising said macromolecular complex can be stored at a temperature of from −70° C. to +4° C. for the liquid forms and up to +40° C. for the solid forms for 3 years.

Moreover, the macromolecular complex obtained according to the method described previously can also be incorporated, as an ingredient, into food compositions.

Consequently, a subject of the invention is also a food composition comprising at least the macromolecular complex and at least one food ingredient. The food ingredient may be, for example, a milk preparation, cereals, etc.

Such a food composition can be intended for humans or animals and can in particular be in the form of dietetic or nondietetic food products for hospital or non-hospital use. In particular, this composition may be an enteral solute.

The weight concentration of said macromolecular complex represents from 10 ng/g to 2 µg/g, preferably from 10 ng/g to 1 µg/g of the food composition.

Finally, the macromolecular complex obtained according to the method described previously can be incorporated, as a food ingredient, into nutraceutical compositions.

A subject of the invention is therefore a nutraceutical composition comprising at least said macromolecular complex and at least a nutraceutically acceptable support.

The weight concentration of said macromolecular complex represents from 10 ng/g to 5 µg/g of the nutraceutical composition.

The term "nutraceutical composition" is intended to mean a composition which has beneficial or protective physiological effects greater than those that conventional nutrition could provide.

Such a nutraceutical composition can be in the form of food supplements. These food supplements can be in solid form, such as tablets, powders, gel capsules or capsules, or in liquid form, such as beverages or emulsions.

The nutraceutical composition according to the invention can therefore be used in order to prevent inflammatory rheumatism, osteoarthritis and fibromyalgia.

The invention therefore relates to the use of said nutraceutical composition for obtaining a food supplement intended for preventing inflammatory rheumatism, osteoarthritis and fibromyalgia.

Thus, the invention relates to a nutraceutical composition for use in the prevention of inflammatory rheumatism, osteoarthritis and fibromyalgia.

BRIEF DESCRIPTION OF THE DRAWINGS

FIG. 6a represents joints of left posterior limbs (which have not undergone an injection of sodium iodoacetate: MIA) of rats belonging to the control group not treated with the macromolecular complex of the invention.

FIG. 6b represents joints of left posterior limbs (which have not undergone injection of MIA) of rats belonging to the group treated with the macromolecular complex of the invention.

FIGS. 7a and 7b represent joints of right posterior limbs (having undergone an injection of MIA) of rats belonging to the control group not treated with the macromolecular complex of the invention.

FIGS. 7c and 7d represent joints of right posterior limbs (having undergone an injection of MIA) of rats belonging to the group treated with the macromolecular complex of the invention.

FIG. 8 represents Table 6, which shows the genes of which the expression is restored to the expression values in human flora-associated mice.

FIG. 9 represents Table 7, which shows the genes of which the expression is modified only with treatment.

Figure 1:
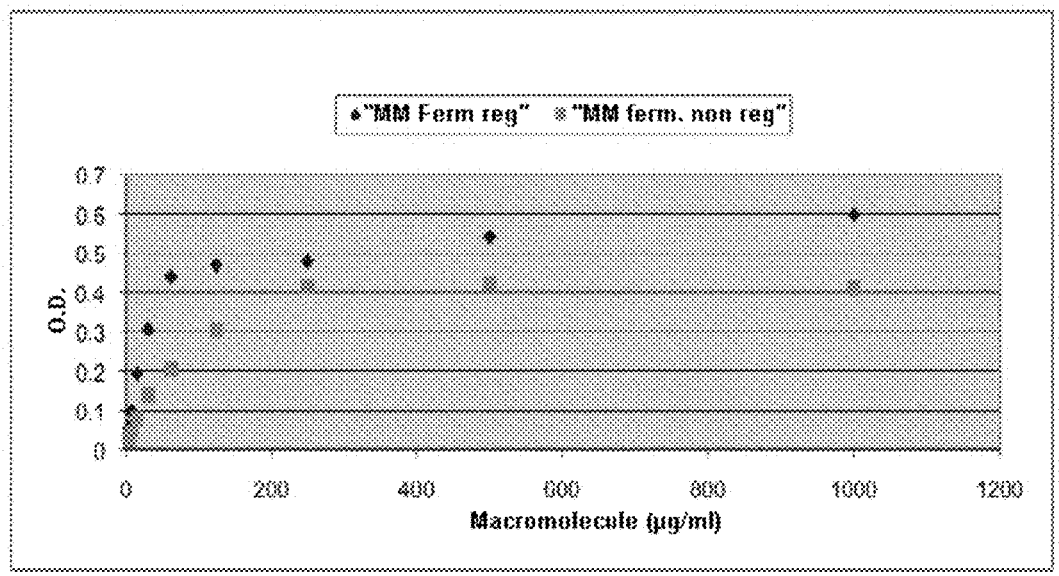
FIG. 1 represents the recognition, in vitro, by galectin-1, of the macromolecular complex obtained with fermentation either with regulated pH or with non-regulated pH according to the invention.

The present invention will be illustrated by the following examples.

EXAMPLES

Example 1

Preparation and Isolation of the Macromolecular Complex According to the Invention (pH Regulated During the Fermentation)

A culture medium containing the following ingredients is prepared:
1 to 20 g/l of a protein base composed of permeate of milk proteins which have been hydrolyzed or are in native form
30 to 80 g/l of lactose
0.1 to 0.5 g/l of ascorbic acid
0.5 to 3 g/l of potassium dihydrogen phosphate.

A first solution is reconstituted with lactose only, and sterilized at 108° C. for 130 minutes. A second solution is reconstituted with the rest of the ingredients and sterilized at 121° C. for 20 minutes.

The fermentation is batch fermentation with pH regulated for 24 hours.

1—Batch Fermentation with pH Regulated:

The pH is adjusted to a value of 6.5 once the two solutions have been poured into the fermenter. The culture medium is inoculated with 6 to 10% (v/v) of a 24 h inoculum containing between $1\times10^6$ and $2\times10^8$ colony-forming units (CFU) of bifidobacteria resulting from the *Bifidobacterium longum* strain deposited under number CNCM I-3994 with the Collection Nationale de Cultures de Microorganismes (CNCM) [National Collection of Microorganism Cultures] per ml of culture medium. The bacteria are cultured with shaking, without aeration of the medium and at a temperature of 37° C. The pH is maintained at 6.5 by adding sodium hydroxide (1 N to 3 N) during the fermentation.

The fermentation lasts 24 hours and the *Bifidobacterium longum* population at the end of the culture is between $2\times10^8$ and $1\times10^{10}$ CFU per ml of culture medium.

2—Isolation of the Macromolecular Complex

At the end of the culture, the bacteria are removed by centrifugation at 13 000 g for 30 minutes at a temperature of 4° C. or by microfiltration on MILLISTAK® cassettes (Millipore) having a surface area suitable for the fermentation volume.

The supernatant is ultrafiltered at ambient temperature and under sterile conditions on an AMICON® PROFLUX® M12 apparatus (Millipore). A first ultrafiltration is performed on a Helicon spiral-wound cartridge (Millipore) with a cutoff threshold 10 kDa.

The supernatant is concentrated at most 15-fold, then washed continuously with sterile osmosed water, 30 times the concentration volume. The 10 kDa retentate recovered is stored at 4° C. or frozen for the second ultrafiltration.

The second ultrafiltration is also carried out at ambient temperature and under sterile conditions on the same apparatus as previously, but equipped with a support for PELLICON® cassettes (Millipore). The cassette used is of BIOMAX® type, with a surface area of 0.5 m² and a cutoff threshold of 100 kDa. The 10 kDa retentate is concentrated at most 2-fold and then washed continuously with 30 volumes of osmosed water.

The >100 kDa retentate is stored in frozen or lyophilic form until purification.

The macromolecular complex contained in the >100 kDa retentate is subsequently obtained under sterile conditions by exclusion chromatography on a SUPERDEX® 200 gel (GE Healthcare). The macromolecular complex is thus separated and then eluted in the excluded fraction (>600 kDa) with a Tris/50 mM HCl-150 mM NaCl buffer, pH 8.0.

This excluded fraction is then desalified by filtration, then diafiltered with 5 to 7 volumes of sterile osmosed water. The macromolecular complex is thus recovered and stored in a lyophilic form.

Example 2

Preparation and Isolation of the Macromolecular Complex According to the Invention (pH not Regulated During the Fermentation)

The composition of the culture medium and the steps are the same as in example 1, with the exception that, in this example, the pH is not regulated during the fermentation, step 1 is thus replaced with the step described below.

1—Batch Fermentation with pH not Regulated During the Fermentation:

The pH is adjusted to a value of 6.5 once the two solutions have been poured into the fermenter. The culture medium is inoculated with 6 to 10% (v/v) of a 24 h inoculum, containing between $1\times10^6$ and $2\times10^8$ colony-forming units (CFU) of bifidobacteria resulting from the *Bifidobacterium longum* strain deposited under number CNCM I-3994 with the Collection Nationale de Cultures de Microorganismes (CNCM) [National Collection of Microorganism Cultures] per ml of culture medium. The bacteria are cultured with shaking, without aeration of the medium and at a temperature of 37° C. The pH is not adjusted during the fermentation. The fermentation lasts 24 hours and the *Bifidobacterium longum* population at the end of the culture is between $1\times10^7$ and $1\times10^9$ CFU per ml of culture medium.

The isolation of the macromolecular complex can be subsequently carried out according to step 2 of example 1.

In the remainder of this text, C1 refers to the macromolecular complex prepared according to example 2 of the invention.

Example 3

Characterization of the Macromolecular Complex

The saccharide, protein and lipid components which make up the macromolecular complex were characterized qualitatively and quantitatively using various analytical methods.

The protein concentration was determined by the Lowry method. It is from 80 to 400 µg/mg of powder (8 to 40% of the macromolecular complex).

The saccharide concentration was determined by gas chromatography after methanolysis (MeoH/HCl at 0.5 N), then derivation with heptafluorobutyric anhydride (20 µl in 100 µl of anhydrous acetonitrile). It is from 20 to 150 µg/mg of powder (2 to 15% of the macromolecular complex).

lipoprotein: the sequence SEQ ID No. 2 is the following:

MTNVRVIKPALAALVAAAACVGGLAFSSAQPAQADTYSDLINAQNQHAASVQREAELKQ

QLAGASQDLANKVLELDDLTNNKIVAAQAKVTQANEDAATAQDEADAASGRLSAAQKDK

ETLEEQIKQTGKDYDDAHAAVAQLARDEMHGSNASDVMSVVTGATSTQDFVNSMQSRDA

LSRNEANAASSAATSLSTSKNRGERLAAIEKQIAVLKTQADEKAASAQTAAETAQSERD

ALDKLRQEGEARRDELSSMIDSLDSQSAKQAAQTVLIASQVDSYNRQFQKEQQDAANRV

DTGNQGGTPSTPVTPAPAPAPAPAPAPAPAPAPSVGGQGTSNGDYGNAYATGQCTYWAY

ERRRQMGIGTPSYLGNGGDWWRNAPSYGLRVDHNPQVGAALSFLPGQDGADGTWGHVAV

VEAVYGDGTFQISEMNVGGLWMMNYRTLTNLGQYWFVH.

Furthermore, the lipid composition established by gas chromatography mass spectrometry shows the presence of major peaks of fatty acids of length C14:0, C16:0 and C18:0.

sugar: the saccharide component of the macromolecule contains the saccharides mentioned in table 1 according to the following molar ratios:

TABLE 1

Weight distribution of sugars which are part of the composition of the macromolecular complex

| | Gal | Man | Glc | Gal NAc | Glc NAc | Rham |
|---|---|---|---|---|---|---|
| Weight composition (µg/mg of macromolecular complex) | 15.35 | 4.95 | 35.10 | 6.75 | 1.5 | 1.45 |

The macromolecular complex is recognized in vitro by galectin-1 (FIG. 1).

In the present example, the macromolecular complex of the present invention and resulting from the fermentation with pH regulated or not regulated is recognized, after adsorption in microplate wells, by galectin-1 (visualization using the biotin-streptavidin system). According to FIG. 1, saturation is observed for concentrations of about from 10 to 20 µg of macromolecular complex per 10 ng of galectin-1.

Figure 2:
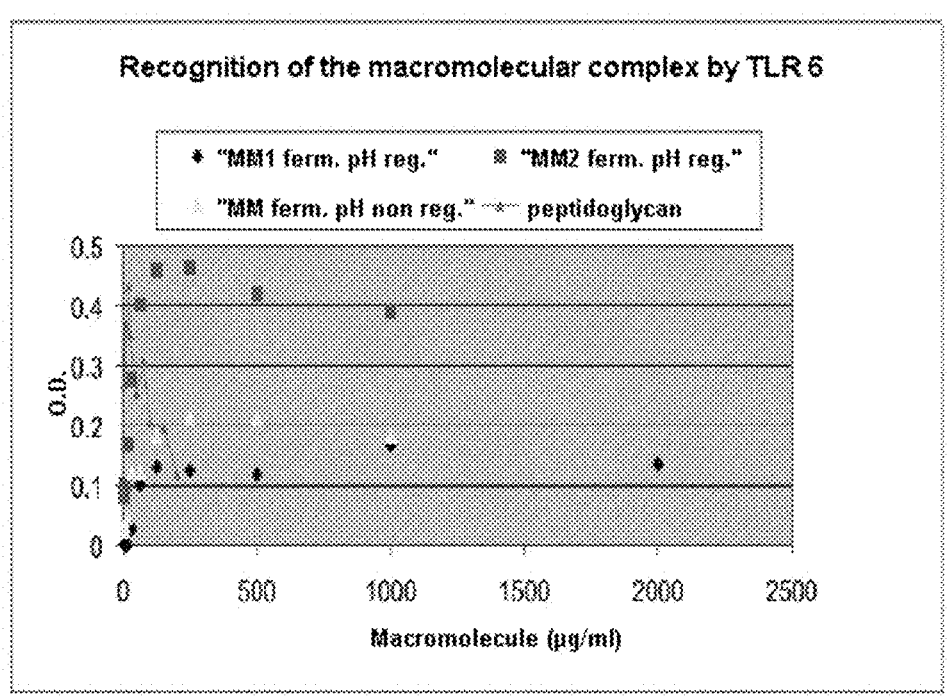
FIG. 2 represents the recognition, in vitro, by TLR-6 of the macromolecular complex obtained with fermentation either with regulated pH or with non-regulated pH according to the invention.

The macromolecular complex is recognized, in vitro, by TLR-6 (FIG. 2).

In the present example, the macromolecular complex of the present invention resulting from fermentation with pH regulated or not regulated is recognized, after adsorption in microplate wells, by TLR6 (visualization using the biotin-streptavidin system). According to FIG. 2, saturation is observed for concentrations of about from 10 to 20 µg of macromolecule per 10 ng of TLR6. The expression in terms of peptidoglycan unit is approximately from 0.2 to 0.4 µg of peptidoglycan per 1 µg of macromolecule.

Example 4

Effect of the Macromolecular Complex C1 in Mice with an Arthritic Patient Flora For this study, the mice used were divided into two groups:
a test group in which axenic mice were associated with the flora of a patient suffering from progressive arthritis (FA);
a control group in which axenic mice were inoculated with the flora of a healthy volunteer (FN).

The descendants from the first to the fourth generation were used for the study.

The macromolecular complex C1 [pH not regulated] was administered orally for 15 days at a dose of 0.2 mg/l (the average dose taken per mouse is between 25-50 µg/kg).

The mice, which had not eaten since the previous day, were euthanized. The spleen was removed aseptically and treated with collagenase in order to release the splenocytes. The CD11c dendritic cells, and the CD4(+) Th and Treg. lymphocytes were isolated using the MACs system. The intestinal flora was analyzed in the ileum, the cecum and the colon. The bacterial translocation was evaluated by bacteriological analysis of the Peyer's patches, the liver, the lung, the kidneys and the blood.

The results are collated in table 2 and clearly demonstrate an increase in the level of bifidobacteria along the intestine of the mice treated with C1, and thus show the beneficial effect of the administration of the latter on the intestinal flora.

TABLE 2

Effect of administration of the macromolecular complex C1 on the intestinal flora.

| | control | test | p |
|---|---|---|---|
| Mice (n) | 6 | 5 | |
| ileum | | | |
| E. coli | 5.38 ± 0.6 (5) | 4.89 ± 1.3 (5) | NS |
| Bifidobacteria | 2.68 ± 0.7 (2) | 3.49 ± 1.7 (5) | 0.0398 |
| cecum | | | |
| E. coli | 7.89 ± 0.3 (6) | 7.52 ± 0.4 (5) | NS |
| Bifidobacteria | 3.06 ± 0.4 (3) | 6.43 ± 1.5 (5) | 0.0061 |

TABLE 2-continued

Effect of administration of the macromolecular complex C1 on the intestinal flora.

|  | control | test | p |
|---|---|---|---|
| colon |  |  |  |
| E. coli | 7.61 ± 1.4 (6) | 8.11 ± 0.4 (5) | NS |
| Bifidobacteria | 3.0 ± 0.8 (6) | 6.56 ± 1.5 (5) | 0.0057 |

Example 5

Involvement of Intestinal Bacteria in Arthritis in DBA1 Mice and Effect of the Macromolecular Complex C1 of the Invention For this study, two models were established according to the type of injection selected:
  model 1: two doses of collagen, three weeks apart, are injected into DBA1 mice;
  model 2: a cocktail of anti-collagent antibodies (MD Biosciences) followed by an injection three days later of LPS (lipopolysaccharide) are injected into DBA1 mice.

Regardless of the model, these injections induce a clinical picture which is suggestive of RA (rheumatoid arthritis). The arthritis score is established by estimating the redness and swelling of the paws.

Figure 3:
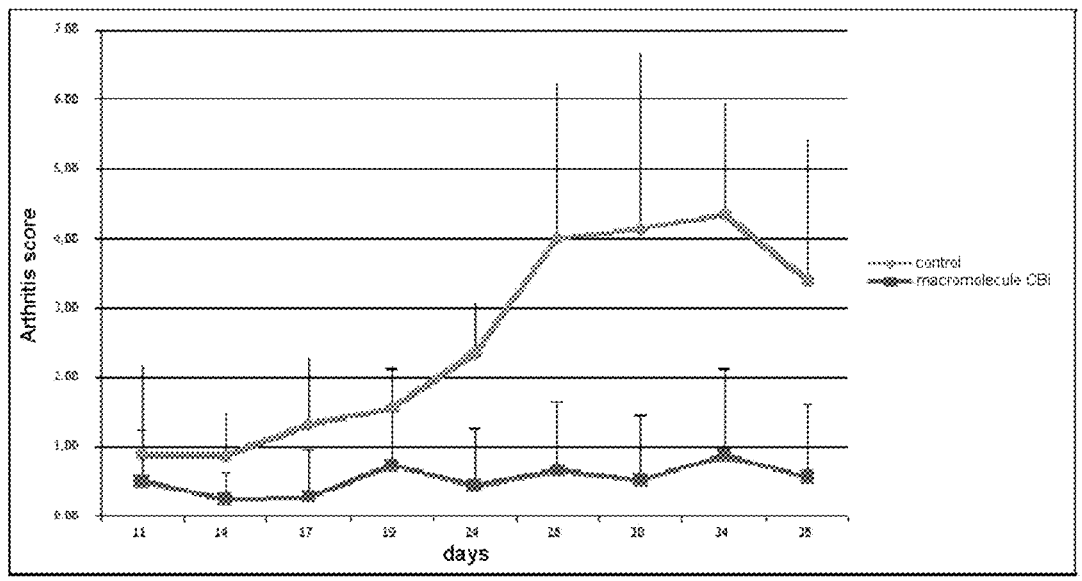
FIG. 3 represents the arthritis score in DBA1 mice after two collagen injections with or without treatment with the macromolecular complex prepared according to example 2 (0.2 mg/l, i.e. 30-40 µg/kg).
Figure 4:
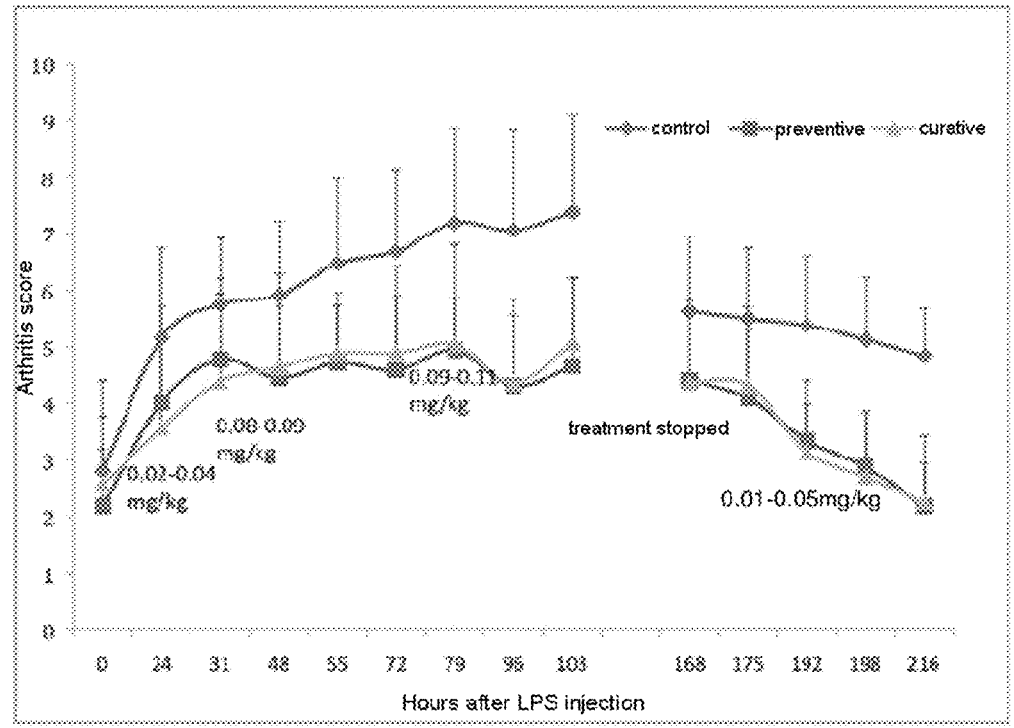
FIG. 4 represents the progression of arthritis induced by a cocktail of antibodies and LPS in DBA1 mice.

The treatment with the macromolecular complex C1 is initiated either 15 days before the first injection of the inducer (model 1—FIG. 3), or upon appearance of the symptoms (model 2—FIG. 4). The concentrations of the macromolecular complex C1 range between 0.1 mg/l and 0.5 mg/l, i.e. estimated daily doses between 10 and 100 µg/kg of body weight.

The effective dose is located within a range of from 30 to 90 µg/kg depending on the arthritis-inducing model (FIGS. 3 and 4).

The score increases approximately ten days after the second injection of collagen in the first model and 3-4 days after the injection of LPS in the second case.

After three days without treatment (model 2), the treatment is again administered (in a proportion of 0.2 mg/l, i.e. 0.01 to 0.05 mg of the macromolecular complex C1/kg of body weight).

Table 3 represents the concomitant analysis of the intestinal flora and shows that the intensity of the joint inflammation is stronger when the number of splenic dendritic cells is low with treatment with the macromolecular complex C1 of the invention, whereas there is no dependence between the two factors in the absence of treatment.

As it happens, it is observed in the treated mice that the number of splenic dendritic cells is linked not only to a population of lactobacillae (Lb09), but also to the population of *Bacteroides caecaux*. In the absence of treatment, the number of dendritic cells is affected exclusively by populations of lactobacillae. In the two groups of mice, the higher the number of *Lactobacillus* 09 in the colon, the lower the number of dendritic cells harbored by the spleen. However, the correlation between *Lactobacillus* 09 and intensity of joint inflammation becomes significant only when the treatment nullifies the effect of a second population of lactobacillae (*Lactobacillus* 081) on the dendritic cells (table 3).

A correlation is therefore noted between this population of lactobacillae (Lb 081) located in the cecum and Peyer's patches and the intensity of the inflammation in the absence of treatment, whereas no dependance is found with treatment, although the *Lactobacillus* 081 population does not decrease (table 3).

In conclusion, the treatment therefore has no antibacterial effect with respect to the *lactobacillus* population, but influences the metabolic balance of the Lb 081 lactobacillae, one or more of the final products of which could be involved in joint inflammation.

TABLE 3

Correlation between intestinal bacterial populations, arthritis score and dendritic cells according to the treatment

| Location | Bacteria | rs* | p |
|---|---|---|---|
| Control mouse |  |  |  |
|  | vs arthritis score |  |  |
| Small intestine | Lactobacillus reuteri | −0.736 | <0.04 |
|  | Streptococcus sp. | −0.812 | <0.02 |
| Cecum | Lactobacillus sp. 081 | 0.88 | <0.01 |
|  | Bacteroides fragilis | −0.862 | <0.006 |
| Colon | Streptococcus sp. | −0.986 | <0.0004 |
| Peyer's patches | Lactobacillus sp. 081 | 0.88 | <0.01 |
|  | Streptococcus sp. | −0.736 | <0.05 |
|  | vs splenic DCs |  |  |
| Small intestine | Lactobacillus sp. 081 | 0.771 | <0.05 |
| Colon | Lactobacillus sp. 09 | −0.829 | <0.01 |
| Mice treated with the macromolecular complex |  |  |  |
|  | vs arthritis score |  |  |
| Cecum | Bacteroides sp. | −0.791 | <0.05 |
| Colon | Lactobacillus sp. 09 | 0.805 | <0.02 |
| Peyer's patches | Lactobacillus sp. 082 | −0.77 | <0.02 |
|  | vs splenic DCs |  |  |
| Cecum | Bacteroides fragilis |  | <0.05 |
| Colon | Lactobacillus sp. 09 | −0.829** | <0.05 |

*rs = Spearman's coefficient
**correlation arthritis score as a function of the number of dendritic cells rs = −0.812 p < 0.05

Example 6

Importance of the Aggregation of the Chains Constituting the Macromolecular Complex C1 of the Invention This example demonstrates the effect of acid hydrolysis on the anti-arthritic efficacy.

28 mg of the macromolecular complex prepared according to example 2 are diluted in 100 ml of a 70% acetic acid solution. The solution is brought to 75° C. for 100 min. The degradation into low-molecular weight molecules is verified by chromatography on SUPERDEX® 200 (the residual macromolecule concentration is about 2.5%). After lyophilization of the degraded product, which enables the acetic acid to be eliminated, the powder is taken up in an equivalent volume of sterile water for administration to DBA1 mice (model 1).

Figure 5:
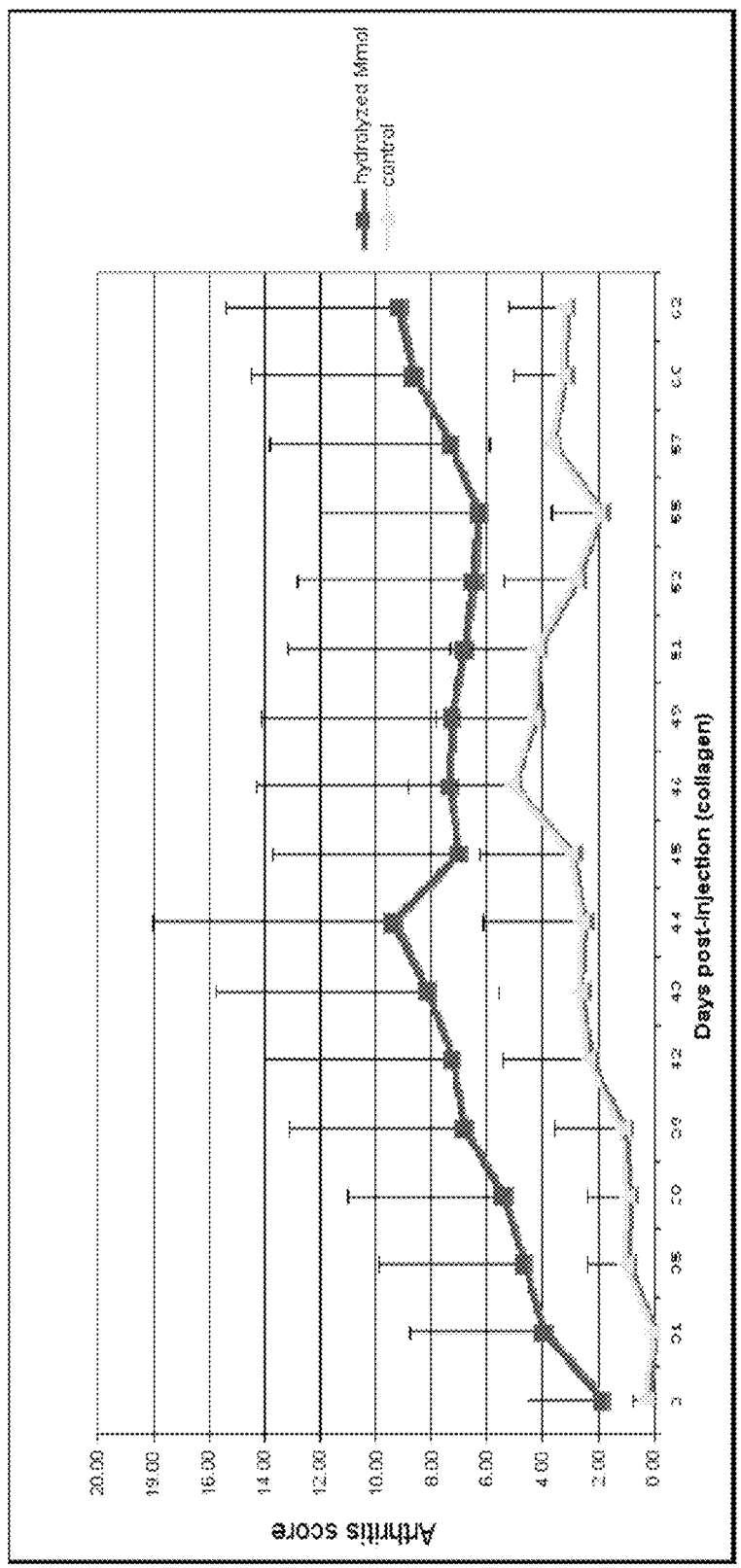
FIG. 5 represents the change in the arthritis score in DBA1 mice treated with the hydrolyzed macromolecular complex (0.2 mg of hydrolyzed macromolecular complex/l).

According to FIG. 5, a pro-arthritic effect is observed, the arthritis scores being higher over time in the group treated with the hydrolyzed macromolecule (two-way repeated measures Anova, $p=5.43852\times10^{-8}$). In conclusion, it is necessary for the units of bifid lipoprotein associated with the oligosaccharides to be aggregated in the form of macromolecules for the anti-arthritic activity to be observed.

Example 7

Comparison Between the Effect of the Administration of the Macromolecular Complex Resulting from the *Bifidobacterium breve* Strain and that Resulting from the *Bifidobacterium longum* Strain Table 4 demonstrates the effect of the treatment with the macromolecular complex resulting from the *Bifidobacterium longum* strain (C1), firstly, and compares the latter with that produced by the administration of the macromolecular complex resulting from *Bifidobacterium breve* (as it is described in WO 2006/040485).

In the remainder of this text, C2 refers to the macromolecular complex prepared according to example 1 of WO 2006/040485.

The experimental protocol is identical to that described in example 4.

The results collated in table 4 show that:
- the number of splenic CD4(+) Th lymphocytes is lower in the mice treated with C2 (macromolecular complex resulting from the *Bifidobacterium breve* strain) compared with the control mice or with those treated with C1 (macromolecular complex resulting from the *Bifidobacterium longum* strain);
- the number of Treg lymphocytes (regulatory cells) is lower in the mice treated with C2 compared with the control mice or with those treated with C1.

These results thus show that the treatment is less effective in the case of the administration of the macromolecular complex resulting from the *Bifidobacterium breve* strain than with the macromolecular complex resulting from the *Bifidobacterium longum* strain deposited under number CNCM I-3994. Indeed, the administration of the complex according to the invention maintains the production of regulatory T cells, these being cells which play a predominant role in the anti-inflammatory response.

TABLE 4

Cell population as a function of the treatment administered

| FA mice (n)* treatment | Dendritic cells CD11c | T lymphocytes Th CD4+ | T lymphocytes Treg CD4+, CD25+ |
|---|---|---|---|
| control (4) | $3.6 \pm 0.9^{a**}$ | $5.30 \pm 0.6$ | $0.32 \pm 0.04$ |
| C1 (4) | $3.04 \pm 0.3$ | $5.2 \pm 0.3$ | $0.30 \pm 0.07$ |
| C2 (4) | $3.28 \pm 0.6$ | $4.07 \pm 1.0$ | $0.22 \pm 0.03$ |

*the mice are of comparable age (approximately 7 months)
$^a$expression as % of splenocytes
**mice associated with flora of a healthy volunteer
CD11c = $4.76 \pm 1.6$ Moreover, table 5 represents Spearman's correlation between the cell populations.

It is demonstrated in this table that the splenic dendritic cell and T lymphocyte levels correlate in the mice treated with the macromolecular complex resulting from the *Bifidobacterium longum* strain C1 (Spearman's correlation close to 1), whereas the cell populations are numerically independent in the mice treated with the macromolecular complex resulting from the *Bifidobacterium breve* strain C2 (Spearman's correlation close to 0).

More specifically, the dendritic cell level in the mice treated with the macromolecular complex resulting from the *Bifidobacterium longum* strain C1 correlates with the sub-population of T lymphocytes, the CD4, CD25 Treg lymphocytes producing the anti-inflammatory interleukin 10. The two cell populations therefore change in a dependent manner with treatment with the macromolecular complex resulting from the *Bifidobacterium longum* strain C1. The macromolecular complex resulting from the *Bifidobacterium longum* strain C1 therefore conditions the dendritic cells, thereby facilitating the recruitment by these cells of the interleukin 10-producing lymphocytes.

TABLE 5

Spearman's correlation between the cell populations according to the treatment

| rs* Treatment | CD11c vs Th CD4+ | p | CD11c vs Th CD4+, CD25+ | p |
|---|---|---|---|---|
| control (9) | 0.45 | NS | 0.45 | NS |
| C1 (7) | 0.81 | <0.05 | 0.79 | <0.05 |
| C2 (7) | 0.16 | NS | 0.07 | NS |

Example 8

Modification of Gene Expression

Tables 6 and 7 demonstrate the effect of the treatment linked to the administration of the macromolecular complex C1 with respect to gene expression by comparing the gene expressions of the dendritic cells of arthritic patient flora-associated mice relative to healthy volunteer flora-associated mice (FA vs FN in table 6) with those of the dendritic cells of arthritic patient flora-associated mice treated for 15 days with 0.2 mg/l of the macromolecular complex C1, relative to non-treated mice (FAt vs FA in table 6). These results show that the hyperstimulation of the flora on the immune system is returned to normal with the treatment.

Indeed, in the case of mice harboring an arthritis flora, a certain number of genes are overexpressed, such as genes for proteolysis or for hydrolysis of sugars, involved in the digestion of the antigens taken up by the dendritic cells, and also genes involved in inflammation (elastase). After treatment (FAt vs FA), an expression similar to that of mice harboring a healthy subject flora is found: by way of example, for elastase, the ratio of FC of its expression in mice harboring the arthritis flora (FA) vs mice harboring a healthy subject flora (FN) (FA vs FN before treatment) is +24.725. After treatment of the mice harboring the arthritis flora with the macromolecular complex C1, the ratio FC comparing its expression with that of the nontreated mice harboring the flora of a patient suffering from arthritis (FAt vs FA) (after treatment) is −23.92, that is to say a return to its baseline expression in a mouse harboring a healthy subject flora.

Moreover, table 7 demonstrates the geners which have not been overactivated by the arthritis flora relative to the healthy subject flora, but the expression of which is all the same modified by the administration of the treatment with C1. For example, the prostaglandin reductase 2 is overexpressed, which suggests a reduction of inflammation. Likewise, the Ednrb gene involved in inflammatory processes is underexpressed following the treatment.

Example 9

Prevention of Chemically Induced Osteoarthritis in Rats by Administration of the Macromolecular Complex Procedure:

Osteoarthritis is induced in male CD-strain rats weighing 125-150 g (Charles River) by injection into the right tibiofemoral joint of 3 mg (0.05 ml of a solution at 60 mg/ml) of sodium iodoacetate (MIA).

The animals are then observed (gradation of limping) for a post-operative period of approximately 15 days before continuously receiving the macromolecular complex resulting from the *Bifidobacterium longum* strain C1 (aqueous solution of 0.3 mg of macromolecular complex resulting from the *Bifidobacterium longum* strain C1/1) per os for 3 weeks (adaptation period).

During the next 5 weeks, the same solution of macromolecular complex resulting from the *Bifidobacterium longum* strain C1 is administered in batchwise fashion (alternating between water for 3-4 days and administration of the solution containing the macromolecular complex C1 for 3-4 days). Thus, the doses received by the rats during the adaptation period are 26.3±7 µg of macromolecular complex C1/kg of body weight, then during the administration period of the next 5 weeks, 18.9±6 µg of macromolecular complex C1/kg of body weight.

At the end of the trial, the rats are euthanized by intraperitoneal injection of sodium pentobarbital (CEVA Santé animale) 2 to 4 hours after having removed the drink and feed.

Moreover, rats which have not received the administration of the macromolecular complex resulting from the *Bifidobacterium longum* strain C1 are also euthanized (control group).

The joints of the posterior limbs of the rats belonging to the group treated with the macromolecular complex resulting from the *Bifidobacterium longum* strain C1 and the rats of the control group are removed and the tibiofemoral articular junction is observed (FIGS. 6 and 7).

In FIGS. 6 and 7, 1 represents the femur, 2 represents the cartilage, 3 represents the synovial membrane, 4 represents the patella and 5 represents the tibia.

Furthermore, a bacteriological analysis is carried out on the following organs: blood, lung, liver, spleen, kidney, Peyer's patches, ileum (three fragments), cecum, colon.

RESULTS

FIGS. 6*a* and 6*b* demonstrate no deformation of the joints of the posterior limbs.

The right posterior limbs (injection of MIA) of the rats not treated with the macromolecular complex C1 show a deformation suggestive of osteoarthritis lesions (FIGS. 7*a* and 7*b*). Conversely, no deformation is noted in rats having received the macromolecular complex C1 (50% of responder rats) (FIGS. 7*c* and 7*d*).

Moreover, the bacteriological analysis makes it possible to establish the following observations. In the responder rats, the intestinal flora is modified in several sites:

staphylococci are undetectable in the distal ileum,
enterobacteria (other than *E. coli*) are undetectable in the colon,
a decrease in clostridia is observed in the cecum (<2.7 vs 3.2±0.5 log cfu/g in the control rats),
a decrease in enterococci is observed in the colon (<5 log cfu/g vs 6.2±0.5 log cfu/g in the control rats).

Moreover, a translocation of lactobacillae in the lungs is noted (4.2±2.5 log cfu/g), whereas the lungs of the unprotected rats are sterile or contaminated with *staphylococci*.

CONCLUSIONS

When the administration of the macromolecular complex of the invention modifies the balance of the intestinal flora in the model of osteoarthritis and the bacterial translocation, it effectively protects the animal against the degenerative process induced by the injection of MIA.

---

The invention claimed is:

1. An isolated bacterial macromolecular complex produced by the *Bifidobacterium longum* strain deposited according to the treaty of Budapest under number CNCM 1-3994, on May 23, 2008, with the Collection Nationale de Cultures de Microorganismes (CNCM) in a culture medium comprising native or hydrolyzed whey proteins, lactose and an antioxidant, the macromolecular complex comprising one or more chains comprising a combination of a lipoprotein and an oligosaccharide, wherein:
the lipoprotein has a molecular weight of from 30 kDa to 60 kDa;
the oligosaccharide has a molecular weight of less than 15 kDa;
the macromolecular complex has a molecular weight of greater than 150 kDa; and
the total amount of lipoprotein is from 75 to 99% by weight of the total weight of the complex, and the
total amount of oligosaccharide is from 1 to 25% of the total weight of the complex.

2. The macromolecular complex as claimed in claim 1, wherein the lipoprotein comprises the amino acid sequence SEQ ID NO: 1.

3. The macromolecular complex as claimed in claim 1, wherein the lipoprotein comprises the amino acid sequence SEQ ID NO: 2.

4. The macromolecular complex as claimed in claim 1, wherein the oligosaccharide comprises at least one saccharide selected from the group consisting of galactose (Gal), N-acetylgalactosamine (Gal Nac), glucose (Glc), N-acetylglucosamine (Glc Nac), rhamnose (Rham), mannose (Man), and mixtures thereof.

5. The macromolecular complex as claimed in claim 4, wherein the average weight composition
of galactose is between 1 and 50 µg/mg of the macromolecular complex,
of mannose is between 0.5 and 10 µg/mg of the macromolecular complex,
of glucose is between 3 and 80 µg/mg of the macromolecular complex,
of N-acetylgalactosamine is between 2 and 30 µg/mg of the macromolecular complex,
of N-acetylglucosamine is between 1 and 10 µg/mg of the macromolecular complex, and
of rhamnose is between 0.05 and 10 µg/mg of the macromolecular complex.

6. The macromolecular complex as claimed in claim 1, wherein the lipoprotein comprises at least one lipid selected from the group consisting of C14, C16, C18 saturated fatty acids and mixtures thereof.

7. A pharmaceutical composition, comprising the macromolecular complex as claimed in claim 1, as active ingredient, and at least one pharmaceutically acceptable support.

8. The pharmaceutical composition as claimed in claim 7, wherein the weight concentration of the macromolecular complex is from 0.1 to 50 µg/g of the pharmaceutical composition.

9. The pharmaceutical composition as claimed in claim 7, configured for use in regulating the intestinal flora and bacterial translocation.

10. The pharmaceutical composition as claimed in claim 7, configured for use in the treatment of inflammatory rheumatism, osteoarthritis and fibromyalgia.

11. A food composition, comprising said macromolecular complex as claimed in claim 1, and at least one food ingredient.

12. A food composition, comprising said macromolecular complex as claimed in claim 1, and at least one food ingredient, wherein the weight concentration of the macromolecular complex is from 10 ng/g to 2 μg/g of the food composition.

13. The food composition as claimed in claim 11, wherein the food composition is in the form of food products.

14. A nutraceutical composition, comprising at least said macromolecular complex as claimed in claim 1, and at least one nutraceutically acceptable support.

15. A nutraceutical composition, comprising said macromolecular complex as claimed in claim 1, and at least one nutraceutically acceptable support, wherein the weight concentration of the macromolecular complex is from 10 ng/g to 5 μg/g of the nutraceutical composition.

16. The nutraceutical composition as claimed in claim 14, wherein the nutraceutical composition is in the form of food supplements.

17. The nutraceutical composition as claimed in claim 14, configured for use in the treatment of inflammatory rheumatism, osteoarthritis and fibromyalgia.

18. The macromolecular complex as claimed in claim 1, having a molecular weight of greater than 400 kDa.

* * * * *

SEQUENCE LISTING

```
<160> NUMBER OF SEQ ID NOS: 2

<210> SEQ ID NO 1
<211> LENGTH: 229
<212> TYPE: PRT
<213> ORGANISM: Bifidobacterium longum

<400> SEQUENCE: 1

Met Thr Asn Val Arg Val Ile Lys Pro Ala Leu Ala Ala Leu Val Ala
1               5                   10                  15

Ala Ala Ala Cys Val Gly Gly Leu Ala Phe Ser Ser Ala Gln Pro Ala
            20                  25                  30

Gln Ala Asp Thr Tyr Ser Asp Leu Ile Asn Ala Gln Asn Gln His Ala
        35                  40                  45

Ala Ser Val Gln Arg Glu Ala Glu Leu Lys Gln Gln Leu Ala Gly Ala
    50                  55                  60

Ser Gln Asp Leu Ala Asn Lys Val Leu Glu Leu Asp Asp Leu Thr Asn
65                  70                  75                  80

Asn Lys Ile Val Ala Ala Gln Ala Lys Val Thr Gln Ala Asn Glu Asp
                85                  90                  95

Ala Ala Thr Ala Gln Asp Glu Ala Asp Ala Ala Ser Gly Arg Leu Ser
```

```
              100                 105                 110
Ala Ala Gln Lys Asp Lys Glu Thr Leu Glu Glu Gln Ile Lys Gln Thr
            115                 120                 125

Gly Lys Asp Tyr Asp Asp Ala His Ala Ala Val Ala Gln Leu Ala Arg
130                 135                 140

Asp Glu Met His Gly Ser Asn Ala Ser Asp Val Met Ser Val Val Thr
145                 150                 155                 160

Gly Ala Thr Ser Thr Gln Asp Phe Val Asn Ser Met Gln Ser Arg Asp
                165                 170                 175

Ala Leu Ser Arg Asn Glu Ala Asn Ala Ala Ser Ser Ala Ala Thr Ser
            180                 185                 190

Leu Ser Thr Ser Lys Asn Arg Gly Glu Arg Leu Ala Ala Ile Glu Lys
        195                 200                 205

Gln Ile Ala Val Leu Lys Thr Gln Ala Asp Glu Lys Ala Ala Pro His
    210                 215                 220

Arg Pro Pro Pro Lys
225

<210> SEQ ID NO 2
<211> LENGTH: 451
<212> TYPE: PRT
<213> ORGANISM: Bifidobacterium longum

<400> SEQUENCE: 2

Met Thr Asn Val Arg Val Ile Lys Pro Ala Leu Ala Ala Leu Val Ala
1               5                   10                  15

Ala Ala Ala Cys Val Gly Gly Leu Ala Phe Ser Ser Ala Gln Pro Ala
                20                  25                  30

Gln Ala Asp Thr Tyr Ser Asp Leu Ile Asn Ala Gln Asn Gln His Ala
            35                  40                  45

Ala Ser Val Gln Arg Glu Ala Glu Leu Lys Gln Gln Leu Ala Gly Ala
        50                  55                  60

Ser Gln Asp Leu Ala Asn Lys Val Leu Glu Leu Asp Asp Leu Thr Asn
65                  70                  75                  80

Asn Lys Ile Val Ala Ala Gln Ala Lys Val Thr Gln Ala Asn Glu Asp
                85                  90                  95

Ala Ala Thr Ala Gln Asp Glu Ala Asp Ala Ala Ser Gly Arg Leu Ser
            100                 105                 110

Ala Ala Gln Lys Asp Lys Glu Thr Leu Glu Glu Gln Ile Lys Gln Thr
        115                 120                 125

Gly Lys Asp Tyr Asp Asp Ala His Ala Ala Val Ala Gln Leu Ala Arg
130                 135                 140

Asp Glu Met His Gly Ser Asn Ala Ser Asp Val Met Ser Val Val Thr
145                 150                 155                 160

Gly Ala Thr Ser Thr Gln Asp Phe Val Asn Ser Met Gln Ser Arg Asp
                165                 170                 175

Ala Leu Ser Arg Asn Glu Ala Asn Ala Ala Ser Ser Ala Ala Thr Ser
            180                 185                 190

Leu Ser Thr Ser Lys Asn Arg Gly Glu Arg Leu Ala Ala Ile Glu Lys
        195                 200                 205

Gln Ile Ala Val Leu Lys Thr Gln Ala Asp Glu Lys Ala Ala Ser Ala
    210                 215                 220

Gln Thr Ala Ala Glu Thr Ala Gln Ser Glu Arg Asp Ala Leu Asp Lys
225                 230                 235                 240
```

-continued

```
Leu Arg Gln Glu Gly Glu Ala Arg Arg Asp Glu Leu Ser Ser Met Ile
            245                 250                 255

Asp Ser Leu Asp Ser Gln Ser Ala Lys Gln Ala Ala Gln Thr Val Leu
            260                 265                 270

Ile Ala Ser Gln Val Asp Ser Tyr Asn Arg Gln Phe Gln Lys Glu Gln
            275                 280                 285

Gln Asp Ala Ala Asn Arg Val Asp Thr Gly Asn Gln Gly Gly Thr Pro
            290                 295                 300

Ser Thr Pro Val Thr Pro Ala Pro Ala Pro Ala Pro Ala Pro Ala Pro
305                 310                 315                 320

Ala Pro Ala Pro Ala Pro Ala Pro Ser Val Gly Gly Gln Gly Thr Ser
                    325                 330                 335

Asn Gly Asp Tyr Gly Asn Ala Tyr Ala Thr Gly Gln Cys Thr Tyr Trp
            340                 345                 350

Ala Tyr Glu Arg Arg Arg Gln Met Gly Ile Gly Thr Pro Ser Tyr Leu
            355                 360                 365

Gly Asn Gly Gly Asp Trp Trp Arg Asn Ala Pro Ser Tyr Gly Leu Arg
            370                 375                 380

Val Asp His Asn Pro Gln Val Gly Ala Ala Leu Ser Phe Leu Pro Gly
385                 390                 395                 400

Gln Asp Gly Ala Asp Gly Thr Trp Gly His Val Ala Val Val Glu Ala
                    405                 410                 415

Val Tyr Gly Asp Gly Thr Phe Gln Ile Ser Glu Met Asn Val Gly Gly
                    420                 425                 430

Leu Trp Met Met Asn Tyr Arg Thr Leu Thr Asn Leu Gly Gln Tyr Trp
            435                 440                 445

Phe Val His
        450
```